United States Patent
Goto

(10) Patent No.: US 12,020,431 B2
(45) Date of Patent: Jun. 25, 2024

(54) IMAGE PROCESSING APPARATUS AND ULTRASONIC DIAGNOSTIC APPARATUS

(71) Applicant: CANON MEDICAL SYSTEMS CORPORATION, Otawara (JP)

(72) Inventor: Kota Goto, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 330 days.

(21) Appl. No.: 17/446,475

(22) Filed: Aug. 31, 2021

(65) Prior Publication Data

US 2022/0067932 A1 Mar. 3, 2022

(30) Foreign Application Priority Data

Sep. 2, 2020 (JP) ................................. 2020-147657

(51) Int. Cl.
G06T 7/00 (2017.01)
A61B 8/08 (2006.01)
G06T 5/70 (2024.01)
G06T 15/00 (2011.01)

(52) U.S. Cl.
CPC .......... *G06T 7/0012* (2013.01); *A61B 8/5207* (2013.01); *G06T 5/70* (2024.01); *G06T 15/00* (2013.01); *G06T 2207/10132* (2013.01)

(58) Field of Classification Search
None
See application file for complete search history.

(56) References Cited

U.S. PATENT DOCUMENTS

| 8,202,221 B2 | 6/2012 | Osumi et al. |
| 2010/0228129 A1* | 9/2010 | Osumi ................ A61B 8/4483 600/443 |
| 2012/0041312 A1* | 2/2012 | Nakahira ................ G06T 5/50 600/443 |
| 2014/0288426 A1 | 9/2014 | Ebisawa |

FOREIGN PATENT DOCUMENTS

| JP | 2014-184073 A | 10/2014 |
| JP | 2018-139686 A1 | 9/2018 |
| WO | WO 2008/010375 | 1/2008 |

OTHER PUBLICATIONS

Office Action issued Feb. 13, 2024 in Japanese Patent Application No. 2020-147657.

* cited by examiner

*Primary Examiner* — Leon Flores
(74) *Attorney, Agent, or Firm* — Oblon, McClelland, Maier & Neustadt, L.L.P.

(57) ABSTRACT

The image processing apparatus according to any of embodiments includes processing circuitry. The processing circuitry is configured to acquire image data depicting an inside of a subject acquired by an ultrasonic scan. The processing circuitry is configured to perform image processing on the image data, thereby synthesizing the image data before the image processing and the image data after the image processing by changing a synthesis rate for each image portion.

8 Claims, 8 Drawing Sheets

IMAGE PROCESSING APPARATUS AND ULTRASONIC DIAGNOSTIC APPARATUS

CROSS-REFERENCE TO RELATED APPLICATION

This application is based upon and claims the benefit of priority from Japanese Patent Application No. 2020-147657, filed on Sep. 2, 2020, the entire contents of which are incorporated herein by reference.

FIELD

Any of embodiments disclosed in specification and drawings relates to an image processing apparatus and an ultrasonic diagnostic apparatus.

BACKGROUND

In the medical field, an ultrasonic diagnostic apparatus is used for imaging the inside of a subject using ultrasonic waves generated by multiple transducers (piezoelectric vibrators) of an ultrasonic probe. The ultrasonic diagnostic apparatus causes the ultrasonic probe, which is connected to the ultrasonic diagnostic apparatus, to transmit ultrasonic waves into the subject, generates an echo signal based on a reflected wave, and acquires a desired ultrasonic image based on the echo signal by image processing.

In the ultrasonic diagnostic apparatus, various image processings are performed on the image data. Image processing on image data is performed for the purpose of improving the efficiency of diagnosis by improving the visibility of the structure in the image data, reducing noise, and applying speckle reduction effect. Further, if only the image data that has undergone image processing is output, there may be a sense of incongruity. Therefore, the unprocessed image data and the processed image data are synthesized such that a sense of incongruity can be reduced.

DETAILED DESCRIPTION

An image processing apparatus and an ultrasonic diagnostic apparatus according to any of embodiments will be described with reference to the accompanying drawings.

The image processing apparatus according to any of embodiments includes processing circuitry. The processing circuitry is configured to acquire image data depicting an inside of a subject acquired by an ultrasonic scan. The processing circuitry is configured to perform image processing on the image data, thereby synthesizing the image data before the image processing and the image data after the image processing by changing a synthesis rate for each image portion.

The image processing apparatus according to any of embodiments is provided as a part of a medical image diagnostic apparatus that generates a medical image. Hereinafter, in the first embodiment, a case where the image processing apparatus is provided as a part of the ultrasonic diagnostic apparatus, which is a medical image diagnostic apparatus, will be described. Further, in the second embodiment, a case where the image processing apparatus is provided outside the ultrasonic diagnostic apparatus will be described.

First Embodiment

Figure 1:
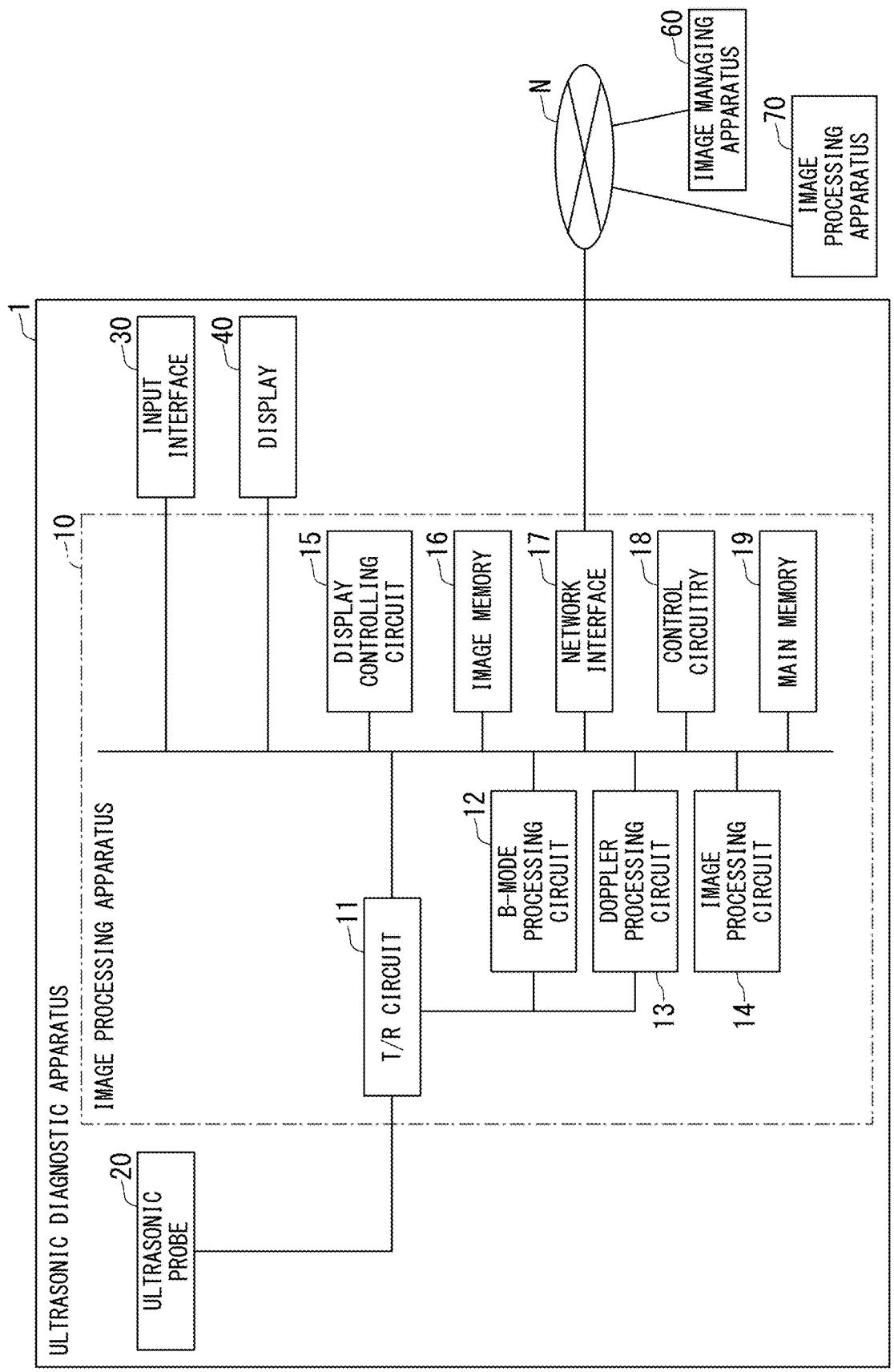
FIG. 1 is a schematic view showing an example of a configuration of an ultrasonic diagnostic apparatus provided with an image processing apparatus according to the first embodiment.

FIG. 1 is a schematic view showing an example of a configuration of an ultrasonic diagnostic apparatus provided with an image processing apparatus according to the first embodiment.

FIG. 1 shows an ultrasonic diagnostic apparatus 1 including an image processing apparatus 10 according to the first embodiment. As shown in FIG. 1, the ultrasonic diagnostic apparatus 1 includes an ultrasonic probe 20, an input interface 30, and a display 40 in addition to the image processing apparatus 10. Note that an apparatus in which at least one of the ultrasonic probe 20, the input interface 30 and the display 40 being added to the image processing apparatus 10 may be referred to as "image processing apparatus". In the following description, a case will be described where the ultrasonic probe 20, the input interface 30 and the display 40 are all provided outside the image processing apparatus 10.

The image processing apparatus 10 includes a transmitting/receiving (T/R) circuit 11, a B-mode processing circuit 12, a Doppler processing circuit 13, an image processing circuit 14, a display controlling circuit 15, an image memory 16, a network interface 17, control circuitry 18, and a main memory 19. The circuits 11 to 15 are configured by application-specific integrated circuits (ASICs) and the like. However, the present invention is not limited to this case, and all or part of the functions of the circuits 11 to 15 may be realized by the control circuitry 18 executing a program.

The T/R circuit 11 has a transmitting circuit and a receiving circuit (both not shown). Under the control of the control circuitry 18, the T/R circuit 11 controls transmission directivity and reception directivity in transmitting and receiving ultrasonic waves. The case where the T/R circuit 11 is provided in the image processing apparatus 10 will be described, but the T/R circuit 11 may be provided in the ultrasonic probe 20, or may be provided in both of the image processing apparatus 10 and the ultrasonic probe 20. The T/R circuit 11 is one example of a transmitting/receiving unit.

The transmitting circuit, which has a pulse generating circuit, a transmission delay circuit, a pulsar circuit, and the like, supplies a drive signal to ultrasonic transducers of the ultrasonic probe 20. The pulse generating circuit repeatedly generates rate pulses for forming transmission ultrasonic waves at a predetermined rate frequency. The transmission delay circuit converges the ultrasonic waves generated from the ultrasonic transducer of the ultrasonic probe 20 into a beam shape, and gives a delay time of each piezoelectric transducer necessary for determining the transmission directivity to each rate pulse generated by the pulse generating circuit. The pulsar circuit applies drive pulses to each ultrasonic transducer at a timing based on the rate pulses. The transmission delay circuit arbitrarily adjusts the transmission direction of the ultrasonic beam transmitted from a piezoelectric transducer surface by changing the delay time given to each rate pulse.

The receiving circuit, which has an amplifier circuit, an analog to digital (A/D) converter, an adder, and the like, receives the echo signal received by the ultrasonic transducers, and generate echo data by performing various processes on the echo signal. The amplifier circuit amplifies the echo signal for each channel, and performs gain correction processing. The A/D converter A/D-converts the gain-corrected echo signal, and gives a delay time necessary for determining the reception directivity to the digital data. The adder adds the echo signal processed by the A/D converter to generate echo data. By the addition processing of the adder, the reflection component from the direction corresponding to the reception directivity of the echo signal is emphasized.

Under the control of the control circuitry 18, the B-mode processing circuit 12 receives the echo data from the receiving circuit, performs logarithmic amplification, envelope detection processing and the like, thereby generating data (two-dimensional (2D) or three-dimensional (3D) data) which signal intensity is represented by brightness of luminance. This data is generally called "B-mode data". The B-mode processing circuit 12 is an example of a B-mode processing unit.

The B-mode processing circuit 12 may change the frequency band to be visualized by changing the detection frequency using filtering processing. By using the filtering processing function of the B-mode processing circuit 12, harmonic imaging such as the contrast harmonic imaging (CHI) or the tissue harmonic imaging (THI) is performed. That is, the B-mode processing circuit 12 may separate the reflected wave data of a subject where the contrast agent is injected into harmonic data (or sub-frequency data) and fundamental wave data. The harmonic data (or sub-frequency data) refers to the reflected wave data having a harmonic component whose reflection source is the contrast agent (microbubbles or bubbles) in the subject. The fundamental wave data refers to the reflected wave data having a fundamental wave component whose reflection source is tissue in the subject. The B-mode processing circuit 12 is able to generate B-mode data for generating contrast image data based on the reflected wave data (received signal) having the harmonic component, and to generate B-mode data for generating fundamental wave image data based on the reflected wave data (received signal) having the fundamental wave component.

In the THI using the filtering processing function of the B-mode processing circuit 12, it is possible to separate harmonic data or sub-frequency data, which is reflected wave data (received signal) having a harmonic component, from reflected wave data of the subject. Then, the B-mode processing circuit 12 generates B-mode data for generating tissue image data in which the noise component is removed from the reflected wave data (received signal) having the harmonic component.

When the CHI or THI harmonic imaging is performed, the B-mode processing circuit 12 may extract the harmonic component by a method different from the method using the above-described filtering. In the harmonic imaging, an amplitude modulation (AM) method, a phase modulation (PM) method, or an AM-PM method combining the AM method and the PM method is performed. In the AM method, the PM method, and the AM-PM method, ultrasonic transmission with different amplitudes and phases is performed multiple times on the same scanning line. Thereby, the T/R circuit 11 generates and outputs multiple reflected wave data (received signal) in each scanning line. The B-mode processing circuit 12 extracts harmonic components from the multiple reflected wave data (received signal) of each scanning line by performing addition/subtraction processing according to the modulation method. The B-mode processing circuit performs envelope detection processing etc. on the reflected wave data (received signal) having the harmonic component to generate B-mode data.

For example, when the PM method is performed, the T/R circuit 11 transmits the ultrasonic waves of the same amplitude and reversed-phase polarities, such as (−1, 1), twice by each scanning line in a scan sequence set by the control circuitry 18. The T/R circuit 11 generates a reception signal based on transmission of "−1" and a reception signal based on transmission of "1". The B-mode processing circuit 12 adds these two reception signals. As a result, a signal in which the fundamental wave component is removed while the second harmonic component mainly remains is generated. Then, the B-mode processing circuit 12 performs envelope detection processing and the like on this signal to generate B-mode data using THI or CHI.

Alternatively, for example, in the THI, an imaging method using the second harmonic component and a difference tone component included in the received signal has been put into practice. In the imaging method using the difference tone component, the transmission ultrasonic waves having, for example, a composite waveform combining a first fundamental waves with a center frequency "f1" and a second fundamental waves with a center frequency "f2" larger than "f1" are transmitted from the ultrasonic probe 20. Such a composite waveform combines a wave form of the first fundamental waves and a waveform of the second fundamental waves whose phases are adjusted with each other, such that the difference tone component having the same polarity as the second harmonic component is generated. The T/R circuit 11 transmits the transmission ultrasonic waves having the composite waveform, for example, twice while inverting the phase. In such a case, for example, the B-mode processing circuit 12 performs an envelope detection processing etc. after extracting a harmonic component in which the fundamental wave component are removed by adding two received signals while the difference tone component and the second harmonic component are mainly left.

Under the control of the control circuitry 18, the Doppler processing circuit 13 frequency-analyzes the phase information from the echo data from the receiving circuit, thereby generating data (2D or 3D data) by extracting multiple moving data of a moving subject such as average speed, dispersion, power, and the like. This data is an example of the raw data, and is generally called "Doppler data". In the specification, the moving subject refers to, for example, blood flow, tissue such as heart wall, or contrast agent. The Doppler processing circuit 13 is an example of a Doppler processing unit.

The B-mode data generated by the B-mode processing circuit 12 and the Doppler data generated by the Doppler processing circuit 13 are ultrasonic image data before the scan conversion processing. On the other hand, the data generated by the display controlling circuit 15 described later is the display image data after the scan conversion processing. The B-mode data and Doppler data are also referred to as "raw data".

The image processing circuit 14 acquires raw data which is image data before scan conversion processing under the control of the control circuitry 18. The image processing circuit 14 executes speckle removal processing (or structure enhancement processing) based on the acquired raw data. Next, the speckle removing processing of the ultrasonic diagnostic apparatus 1 will be described.

Ultrasonic wave is greatly affected by the attenuation of the living body and has frequency-dependent attenuation, so that difference between a shallow image portion and a deep image portion is significant in the ultrasonic image. Further, an image that spreads in a fan shape is generated depending on the type of the ultrasonic probe. As the scanning line density becomes coarser in the deep image portion, the image quality gets coarser as well, which causes a difference in the effect of image processing between the shallow image portion and the deep image portion. Therefore, if the image processing setting is set suitable for the shallow image portion, the image processing applied to the deep image portion may be too much (shown in FIG. 6A). On the other hand, if the setting is set suitable for the deep image portion, the image processing applied to the shallow portion may be too weak. Accordingly, it is difficult to acquire a uniform image quality by perform the same image processing on the entire ultrasonic image.

Therefore, the image processing circuit 14 performs image processing on the raw data, synthesizes the raw data and the image data after the image processing by changing a synthesis rate for each image portion, and makes adjustment. In such manner, the image processing circuit 14 corrects the image difference due to the frequency-dependent attenuation and the difference in the scanning line density.

To be more specific, firstly, the image processing circuit 14 hierarchically decomposes the raw data by the multiresolution analysis in the speckle removal processing, thereby acquiring low-frequency decomposition image data from the first level to the n-th level (where "n" is a natural number of 2 or more) and high-frequency decomposition image data from the first level to the n-th level. Then, the image processing circuit 14 applies a non-linear anisotropic diffusion filtering to the output data from the next lower level or to the low-frequency decomposition image data in the lowermost level. Also, the image processing circuit 14 performs filtering to generate edge information of the signal for each level based on the output data from the next lower level or the low-frequency decomposition image data in the lowermost level.

Moreover, the image processing circuit 14 controls the signal level of the high-frequency resolution image data for each level based on the edge information of each level. Also, the image processing circuit 14 hierarchically decomposes the output data from the non-linear anisotropic diffusion filtering and the output data from the high-frequency level control acquired in each level by the multiresolution analysis. In such manner, the image processing circuit 14 removes speckles by the synergistic effect of the multiresolution analysis and the non-linear anisotropic diffusion filtering. Here, inbelow, in order to provide more concrete explanation, the case where the number "n" of the levels of the multiresolution analysis is "3". However, the value is not limited to this case, and any value may be used as long as it is a natural number of 2 or more.

Figure 2:
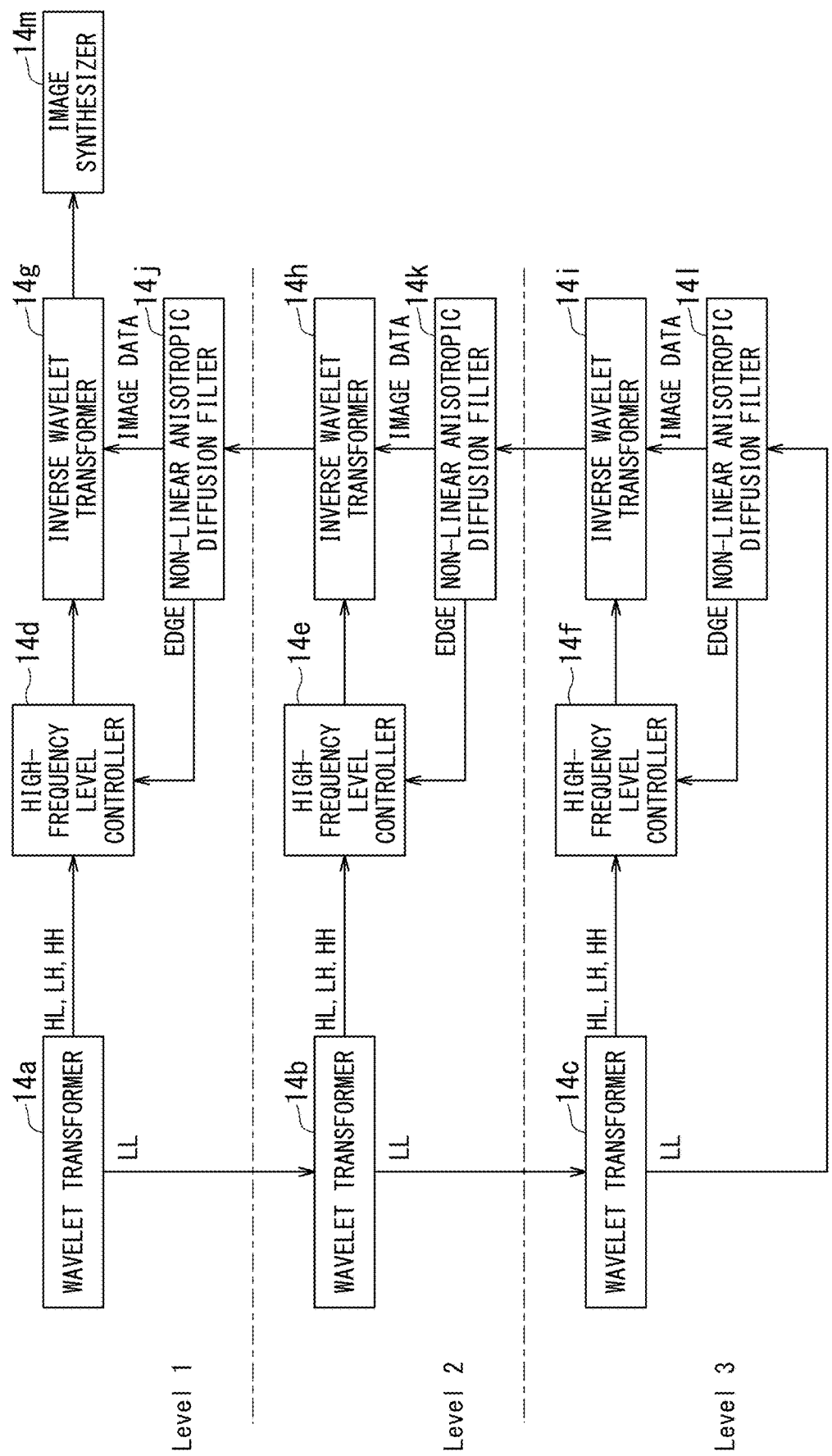
FIG. 2 is a diagram for explaining a speckle removal processing by an image processing circuit of the image processing apparatus according to the first embodiment.

FIG. 2 is a diagram for explaining the speckle removal processing by the image processing circuit 14.

As shown in FIG. 2, the image processing circuit 14 includes wavelet transformers 14a, 14b and 14c, high-frequency level controllers 14d, 14e and 14f, inverse wavelet transformers 14g, 14h and 14i, and non-linear anisotropic diffusion filter 14j, 14k and 14l. First, the level 1 wavelet transformer 14a decomposes the image data (raw data) input from the B-mode processing circuit 12 by the multiresolution analysis. The "wavelet transform" means a discrete wavelet transform. Further, the wavelet transform is only an example for the multiresolution analysis, and the multiresolution analysis is not limited to the wavelet transform. For example, the multiresolution analysis may be realized by another method such as the Laplacian-pyramid method.

As a result of the multiresolution analysis, the image data after decomposition is decomposed into low-frequency image data (LL) which length and width become half of those before decomposition, horizontal high-frequency image data (LH), vertical high-frequency image data (HL), and diagonal high-frequency image data (HH). The low-frequency image data (LL) of the decomposed image data is output to the level 2 wavelet transformer 14b. Further, the horizontal high-frequency image data (LH), the vertical high-frequency image data (HL), and the diagonal high-frequency image data (HH) are output to the high-frequency level controller 14d.

The level 2 wavelet transformer 14b decomposes the low-frequency image data (LL) input from the level 1 wavelet transformer 14a by the multiresolution analysis, thereby acquiring the low-frequency image data (LL), the horizontal high-frequency image data (LH), the vertical high-frequency image data (HL), and the diagonal high-frequency image data (HH). Then, the level 2 wavelet transformer 14b outputs the low-frequency image data (LL) to the level 3 wavelet transformer 14c, and outputs the horizontal high-frequency image data (LH), the vertical high-frequency image data (HL), and the diagonal high-frequency image data (HH) to the high-frequency level controller 14e.

The level 3 wavelet transformer 14c decomposes the low-frequency image data (LL) input from the level 2 wavelet transformer 14b by the multiresolution analysis, thereby acquiring the low-frequency image data (LL), the horizontal high-frequency image data (LH), the vertical high-frequency image data (HL), and the diagonal high-frequency image data (HH). Then, the level 3 wavelet transformer 14c outputs the low-frequency image data (LL) to the level 3 non-linear anisotropic diffusion filter 14l, and outputs the horizontal high-frequency image data (LH), the vertical high-frequency image data (HL), and the diagonal high-frequency image data (HH) to the high-frequency level controller 14f.

Next, the level 3 non-linear anisotropic diffusion filter 14l filters the low-frequency image data (LL), and outputs the filtered low-frequency image data (LL) to the inverse wavelet transformer 14i. The level 3 non-linear anisotropic diffusion filter 14l also generates edge information based on low-frequency image data (LL), and outputs the edge information to the inverse wavelet transformer 14i.

Here, the non-linear anisotropic diffusion filter will be described. The non-linear anisotropic diffusion filter is represented by the following partial differential equation (PDE) (1).

$$\frac{\partial I}{\partial t} = div[D\nabla I] \tag{1}$$

In the above equation (1), "I" indicates the pixel level of the image to be processed, "∇I" indicates the gradient vector, and "t" indicates the time involved in the processing. Further, "D" indicates a diffusion tensor, which can be expressed by the following equation (2).

$$D = \begin{pmatrix} d_{11} & d_{12} \\ d_{12} & d_{22} \end{pmatrix} = R\begin{pmatrix} \lambda 1 & 0 \\ 0 & \lambda 2 \end{pmatrix}R^T \tag{2}$$

In the above equation (2), "R" is a rotation matrix, and the diffusion tensor D indicates a calculation operation in which coefficients λ1 and λ2 are multiplied by a specific direction with respect to the gradient vector and by a direction perpendicular to the specific direction respectively. The direction is the orientation of the detected edges of the image, and the coefficients depend on the size of the edge.

To detect the size and orientation of the edge, the structure tensor of the image is generally acquired, and its eigenvalue and eigenvector are calculated. The eigenvalue is associated with the size of the edge, and the eigenvector represents the orientation of the edge. The structure tensor is defined by the following equation (3).

$$S = G_\rho * \begin{pmatrix} I_x^2 & I_x I_y \\ I_x I_y & I_y^2 \end{pmatrix} = \begin{pmatrix} G_\rho * I_x^2 & G_\rho * (I_x I_y) \\ G_\rho * (I_x I_y) & G_\rho * I_y^2 \end{pmatrix}\begin{pmatrix} S_{11} & S_{12} \\ S_{12} & S_{22} \end{pmatrix} \tag{3}$$

Here, in the above equation (3), "Ix" and "Iy" represent the spatial differentiation of the x (horizontal) direction and the y (vertical) direction of the image to be processed, "Gρ" represents a 2D Gaussian function, and the operator "*" represents convolution. The calculation of edge size and orientation does not necessarily have to strictly follow the above method. Instead of calculating "Ix" and "Iy" as the first step of the processing, a Sobel Filter or a high-frequency component of the multiresolution analysis may be applied.

Since the calculation method of the coefficients λ1 and λ2 in the above equation (2) differs depending on the characteristics of the ultrasonic image in each diagnostic field, it is convenient to prepare a general formula that can be adjusted by some parameters. The calculation of the filter itself is performed by the numerical analysis method of the PDE. That is, at time t, a new pixel level of a point at time t+Δt is calculated based on a pixel of a certain point and each pixel level of multiple points (e.g., 9 points) around the certain point as well as each element value of the diffusion tensor. Next, take t+Δt as a new t and repeat the same calculation once or several times.

Figure 3:
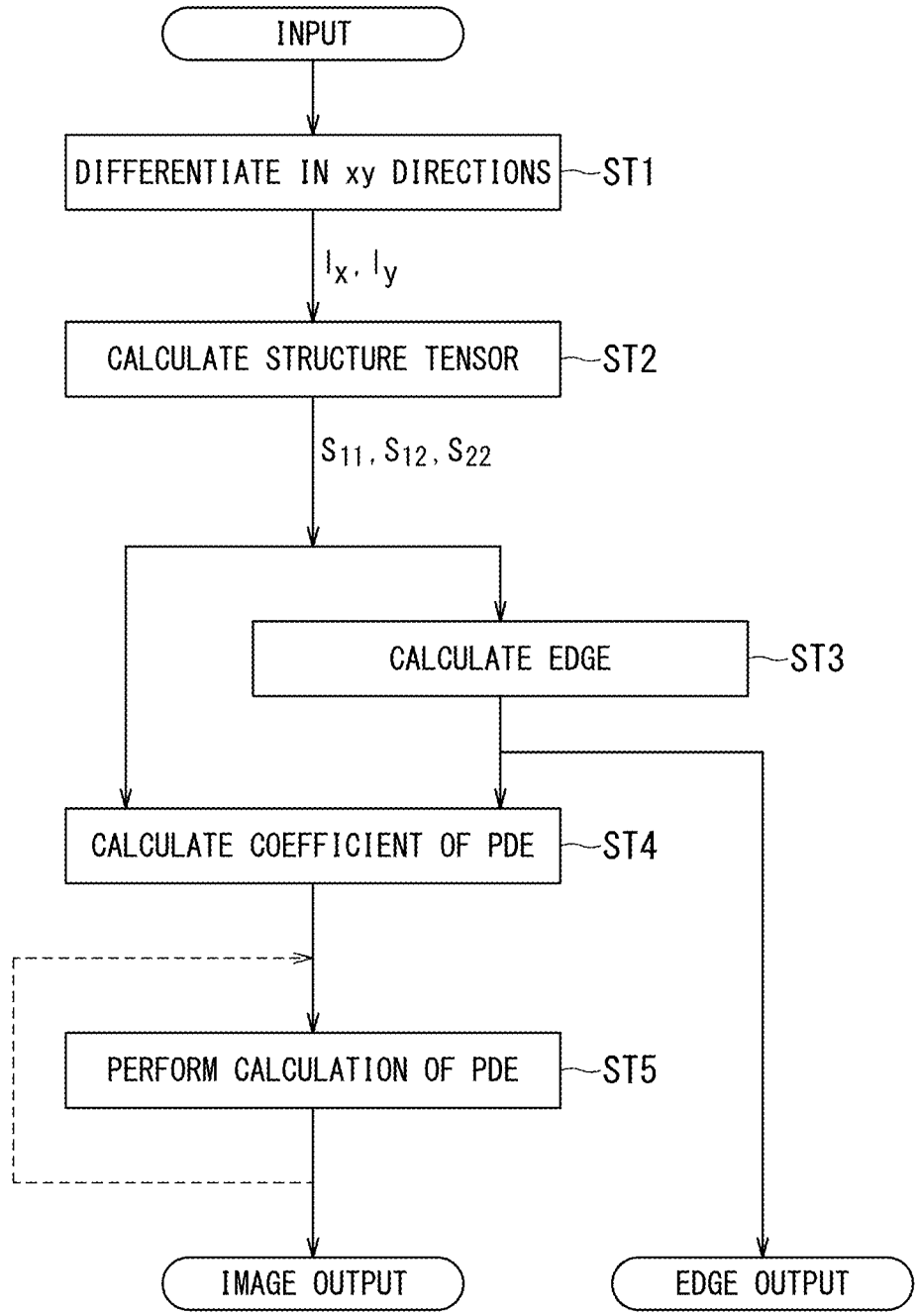
FIG. 3 is a flowchart showing a procedure of the filtering processing using a non-linear anisotropic diffusion filter in the speckle removal processing by the image processing circuit of the image processing apparatus according to the first embodiment.

FIG. 3 is a flowchart showing procedure of the filtering processing of the non-linear anisotropic diffusion filter 14l (or 14j, 14k) in the speckle removal processing by the image processing circuit 14. In FIG. 3, reference numerals with numbers attached to "ST" indicate each step of the flowchart.

As shown in FIG. 3, the non-linear anisotropic diffusion filter 14l differentiates the input low-frequency image data (LL) in the x and y directions (step ST1), and calculates the structure tensors S11, S12 and S22 (step ST2). The calculation in step ST2 also includes the calculation of the Gaussian filter.

Next, the non-linear anisotropic diffusion filter 14l calculates the edge size from each element of the structure tensor (step ST3). This calculation result is applied to the calculation of the PDE in the latter stage and the processing using the high-frequency level controller 14f (or 14d, 14e).

Next, the non-linear anisotropic diffusion filter 14l calculates each coefficient used for numerical analysis of the PDE of the non-linear anisotropic diffusion filter based on each element of the structure tensor (step ST4). In this step, the calculation of the structure tensor is included, and the edge size is also used in the calculation in order to improve the processing efficiency.

Next, the non-linear anisotropic diffusion filter 14l performs the numerical analytical calculation of the PDE once or for several times repeatedly (step ST5). The result acquired by the calculation is output to the inverse wavelet transformer 14i (or 14g, 14h).

Next, as shown in FIG. 2, the level 3 high-frequency level controller 14f inputs the horizontal high-frequency image data (LH), the vertical high-frequency image data (HL), the diagonal high-frequency image data (HH), and edge information on these three components, and controls the high-frequency level accordingly. In the present embodiment, the edge information refers to the result by multiplying the size of the edge standardized based on the eigenvalues of the structure tensor and each pixel of each high-frequency image data to acquire a product respectively, and further multiplying the respect product and the control coefficient of each high-frequency image data. As another example, there is also a method in which a threshold value is set for the size of the edge and the size equal to or above the threshold value is regarded as an edge, while a control coefficient of each high-frequency image data is multiplied by a region other than the edge. The three high-frequency image data processed in this way are input to the inverse wavelet transformer 14i.

The inverse wavelet transformer 14i generates one synthesized image data on the basis of the low-frequency image data (LL) from the non-linear anisotropic diffusion filter 14l, the horizontal high-frequency image data (LH) from the high-frequency level controller 14f, the vertical high-frequency image data (HL) from the high-frequency level controller 14f, and the diagonal high-frequency image data (HH) from the high-frequency level controller 14f. The length and width of the synthesized image is twice that of the input image.

The synthesized image output from the level 3 inverse wavelet transformer 14i is input to the level 2 non-linear anisotropic diffusion filter 14k, subjected to the same filtering processing as in level 3, and then sent to the low-frequency image input of the inverse wavelet transformer

14h. On the other hand, the horizontal high-frequency image data (LH), the vertical high-frequency image data (HL), and the diagonal high-frequency image data (HH) output from the wavelet transformer 14b are subjected to the same high-frequency level control as in the level 3 by the high-frequency level controller 14e, and then sent to the high-frequency image input of the inverse wavelet transformer 14h. Similar to level 3, the inverse wavelet transformer 14h generates one synthesized image data based on one low-frequency image data and three high-frequency image data.

Further, the synthesized image data output from the level 2 inverse wavelet transformer 14h is input to the level 1 non-linear anisotropic diffusion filter 14j, subjected to the same filtering processing as in the levels 2 and 3, and then sent to the low-frequency image input of the inverse wavelet transformer 14g. On the other hand, the horizontal high-frequency image data (LH), the vertical high-frequency image data (HL), and the diagonal high-frequency image data (HH) output from the wavelet transformer 14a are subjected to the same high-frequency level control as in the levels 2 and 3 by the high-frequency level controller 14d, and then sent to the high-frequency image input of the inverse wavelet transformer 14g. The inverse wavelet transformer 14g generates one synthesized image data based on one low-frequency image data and three high-frequency image data in the same manner as in the levels 2 and 3.

As shown in FIG. 2, the image processing circuit 14 further includes an image synthesizer 14m. The image synthesizer 14m acquires image data before the image processing, which is raw data, and image data after the image processing, which is image data after the multiresolution analysis, and divides the image data before the image processing and the image data after the image processing. Then, the image processing circuit 14 synthesizes the image data before the image processing and the image data after the image processing according to the synthesis rate for each image portion to generate the synthesized image data. For example, the image synthesizer 14m divides the image data before the image processing and the image data after the image processing in the depth direction into multiple image portions, and synthesizes the image data before the image processing and the image data after the image processing such that the synthesis rate differs for each image portion to generate the synthesized image data. For example, the image synthesizer 14m makes the synthesis rate of the deep image portion of the image data after the image processing smaller than that of the shallow image portion (closer to the image data before the image processing, which is the original image).

Figure 4:
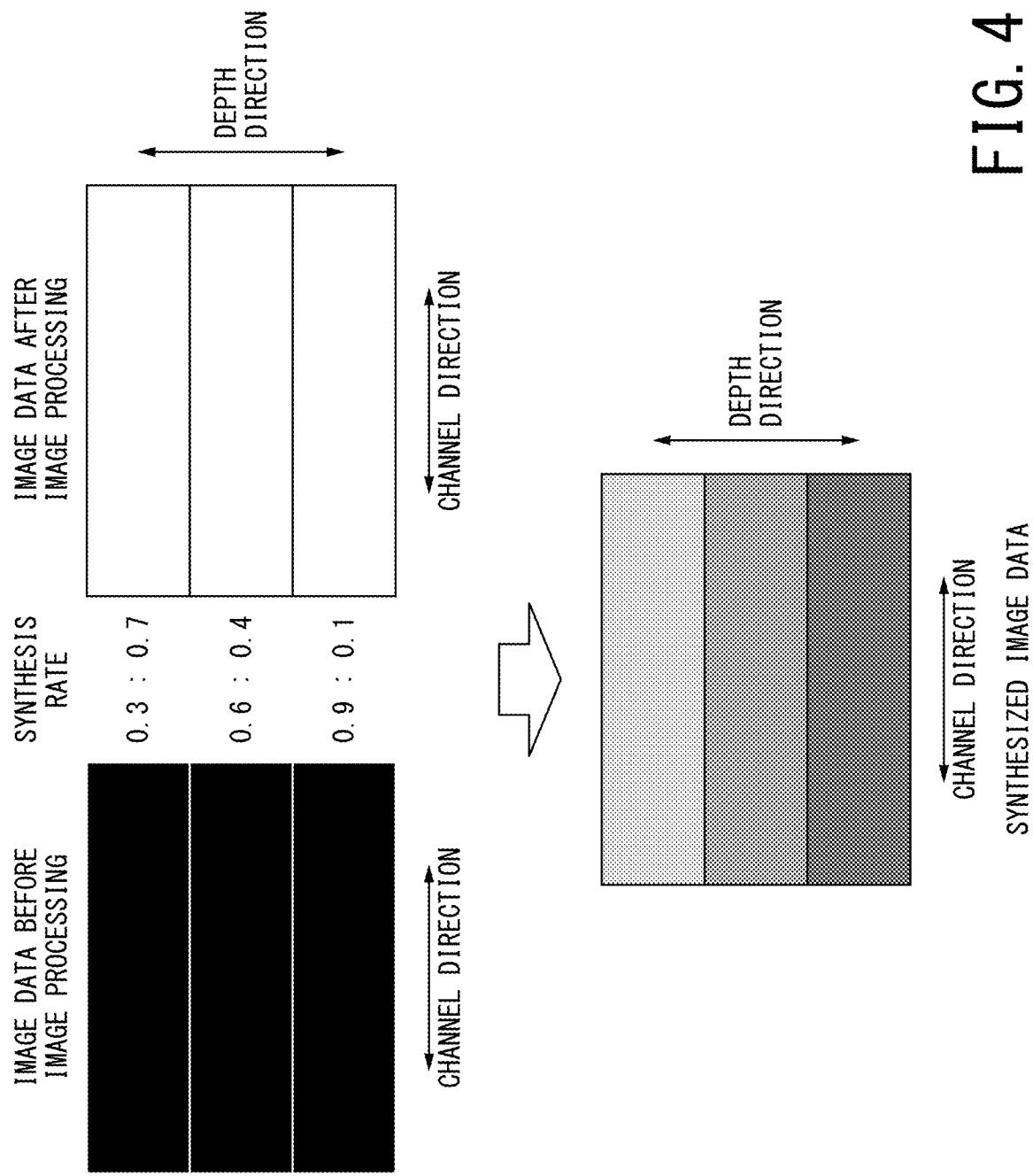
FIG. 4 is a diagram for explaining the synthesizing processing function by the image processing circuit of the image processing apparatus according to the first embodiment.
Figure 5:
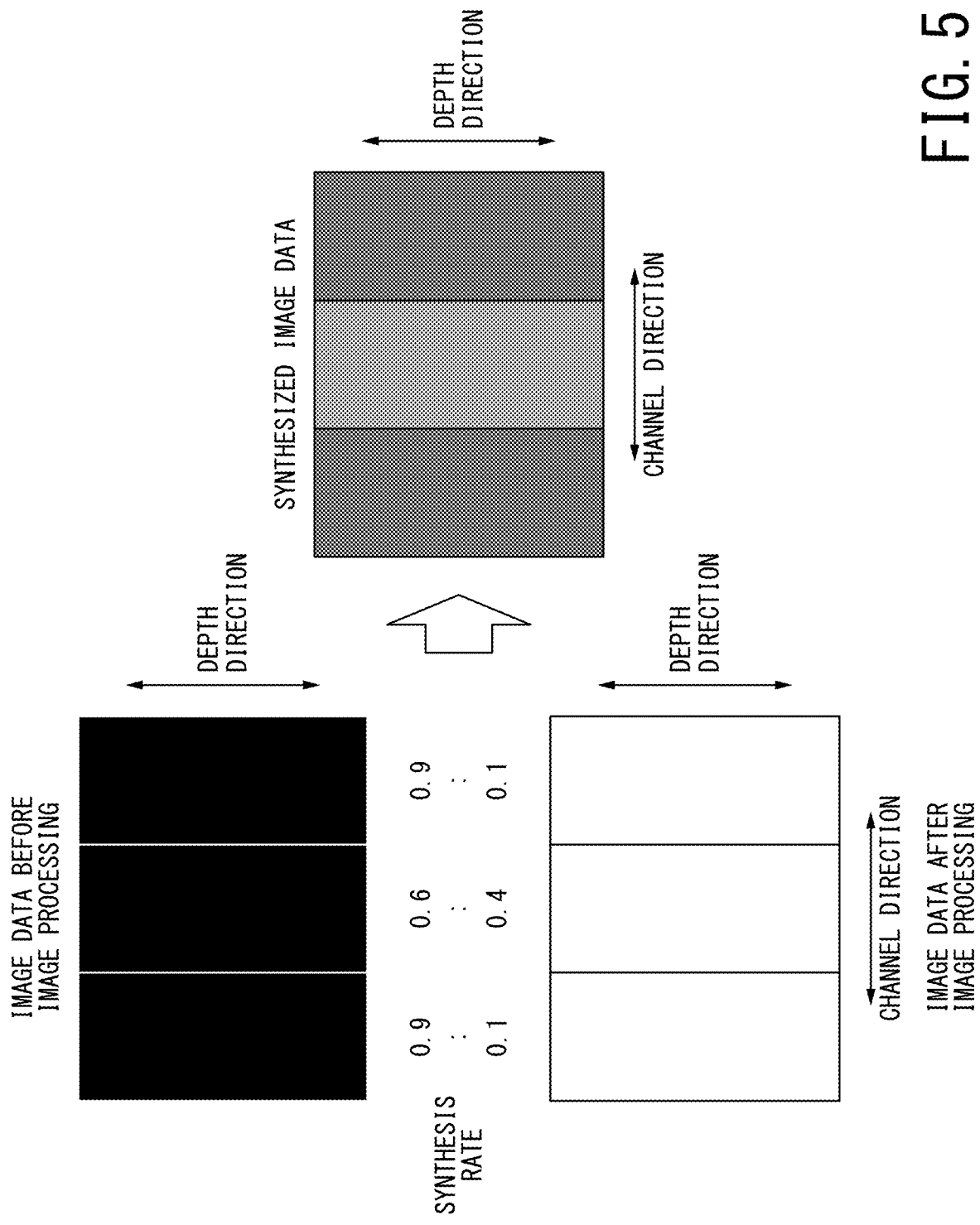
FIG. 5 is a diagram for explaining the synthesizing processing function by the image processing circuit of the image processing apparatus according to the first embodiment.

Each of FIGS. 4 and 5 is a diagram for explaining the synthesizing processing function by the image processing circuit 14.

FIG. 4 shows image data before the image processing and image data after the image processing, which are divided into multiple portions in the depth direction. Here, the entire image data before the image processing is shown in "black", and the entire image data after the image processing is shown in "white" for convenience. Further, each image data is divided into three image portions in the depth direction. Then, the synthesis rate between the image data before and after the image processing is set to "0.3:0.7" for the shallow image portion, "0.6:0.4" for the intermediate image portion, and "0.9:0.1" for the deep image portion.

In this way, each image data is divided into multiple portions in the depth direction, and the image processing settings are changed for each image portion for synthesis, which enables to provide suitable image processing setting for the shallow image portion (shown in light gray close to "white" after the image processing), and suitable image processing setting for the deep image portion (shown in dark gray close to "black" before the image processing). In such manner, even the resolution may differ depending on the depth of each portion due to the attenuation of ultrasonic waves, preferable resolution for each portion having different depths can be adjusted separately. Therefore, uniform synthesized image data can be generated.

The number of divided image portions in each image data is not limited to three as shown in FIG. 4. Further, the size of the image portion is not limited to be uniform as shown in FIG. 4. In addition to what is shown in FIG. 4, the image synthesizer 14m can make the synthesis rate of the deep image portion of the image data after the image processing larger than that of the shallow image portion (closer to the image data after the image processing). Further, it is not limited to the case where the synthesis rate of the image data after the image processing is continuously reduced from the shallow image portion to the deep image portion as shown in FIG. 4. The change in the synthesis rate may be the opposite. Further, it may be a case where the synthesis rate in one or multiple reginal image portions of the image data after the image processing, for example, the central image portion, is made larger (or smaller) than the other image portions. Further, the method is not limited to dividing the image data into multiple of portions in the depth direction. Next, as shown in FIG. 5, an image data may be divided into multiple portions in the channel direction orthogonal to the depth direction.

FIG. 5 shows an image data before the image processing and an image data after the image processing both divided into multiple portions in the channel direction. Here, the entire image data before the image processing is shown in "black", and the entire image data after the image processing is shown in "white" for convenience. Further, each image data is divided into three image portions in the channel direction. Then, the synthesis rate between the image data before and after the image processing is set to "0.6:0.4" for the central image portion, and "0.9:0.1" for the left and right portions.

In this way, each image data is divided into multiple portions in the channel direction, and the image processing settings are set to be different for each image portion, which enables to provide suitable image processing setting for the central image portion (shown in light gray close to "white" after the image processing), and suitable image processing setting for the image portions on both sides (shown in dark gray close to "black" before the image processing). In such manner, even the resolution may differ depending on the distance from the scan center due to the difference in beam density, preferable resolution for each distance can be adjusted separately. Therefore, a uniform synthesized image data can be generated.

The number of divided image portions of the image data is not limited to three as shown in FIG. 5. Further, the size of the image portion is not limited to be uniform as shown in FIG. 5. In addition to what is shown in FIG. 5, the image synthesizer 14m can make the synthesis rate of the left and right image portions of the image data after the image processing larger than that of the central image portion (closer to the image data after the image processing). Further, it is not limited to the case where the synthesis rate in one or multiple local image portions, for example, the central image portion, of the image data after the image processing is made larger than that of the other image portions. The change in the synthesis rate may be the opposite. Further, the synthesis rate may be continuously reduced (or increased) from the left image portion to the right image portion of the image data after the image processing.

Further, the division is not limited to the one-dimensional (1D) division as shown in FIGS. 4 and 5, and may be a 2D division. For example, the division may be a combination of what are shown in FIG. 4 and FIG. 5. In such manner, the resolution can be preferably adjusted separately according to both the depth and the distance from the scan center. Therefore, a more uniform synthesized image data can be generated.

Returning to the description of FIG. 1, the display controlling circuit 15 generally converts (scan-converts) the synthesized image data generated by the image processing circuit 14 into scanning line signal string in a video format typified by a television or the like, thereby generating display image data. Specifically, the display controlling circuit 15 generates display image data by performing coordinate conversion according to the scanning form of ultrasonic waves by the ultrasonic probe 20. In addition to scan conversion, the display controlling circuit 15 performs various image processing such as image processing that regenerates average luminance image using multiple image frames after scan conversion (smoothing processing), image processing using a differential filter in the image (edge enhancement processing), and the like. Further, the display controlling circuit 15 synthesizes the display image data with character information, scales, body marks, and the like of various parameters.

Figure 6A:
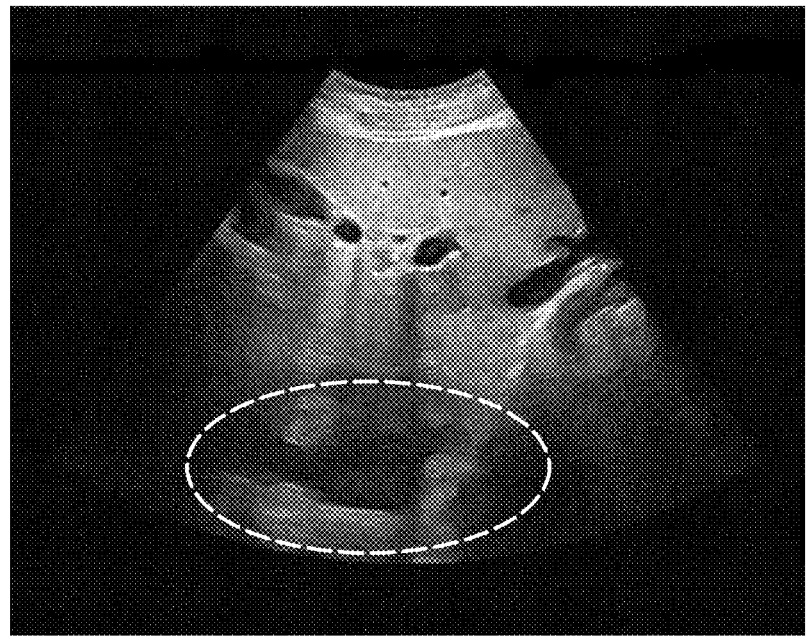
FIG. 6A is a diagram showing a display image data according to a comparative example.
Figure 6B:
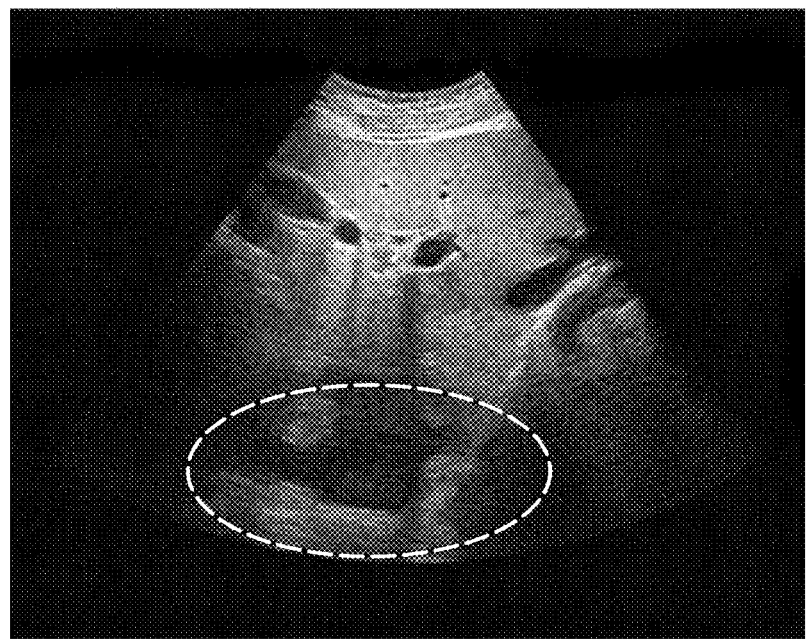
FIG. 6B is a diagram showing display image data according to the first embodiment.

FIG. 6A is a diagram showing a display image data according to a comparative example. FIG. 6B is a diagram showing display image data according to the first embodiment.

FIG. 6A shows ultrasonic image data (display image data), which is the synthesized image data where the image data before the image processing, which is the raw data, and the image data after the image processing are synthesized by the image processing setting suitable for the shallow image portion, and where a scan-converting processing is applied. Since the image processing suitable for the shallow image portion becomes too much for the deep image portion (e.g., a broken line region), there may be a sense of incongruity regarding the deep image portion.

On the other hand, FIG. 6B shows ultrasonic image data (display image data), which is the synthesized image data where the image data before the image processing and the image data after the image processing are synthesized by changing the synthesis rate along the depth direction, and where the scan conversion processing is applied. By setting the image processing suitable for the deep image portion, too much image processing being applied can be prevented, and a sense of incongruity towards the deep image portion can be eliminated.

Returning to the description of FIG. 1, the display controlling circuit 15 can also generate 3D synthesized image data as volume data by performing coordinate conversion on the synthesized image data. Then, the display controlling circuit 15 performs a rendering processing on the volume data in order to generate various 2D image data for displaying the volume data stored in the 3D memory on the display 40. The display controlling circuit 15 performs, for example, a multi planer reconstruction (MPR) processing as a rendering processing to generate MPR image data from the volume data. Further, as the rendering processing, the display controlling circuit 15 performs, for example, a volume rendering (VR) processing for generating 2D image data reflecting 3D information. The display controlling circuit 15 is an example of a display controlling unit.

The image memory 16 has a recording medium, for example, a magnetic or optical recording medium, that can be read by a processor such as a semiconductor memory, or the like. The image memory 16 may store the ultrasonic image data generated by the display controlling circuit 15 as volume data or 2D data under the control of the control circuitry 18. The image memory 16 is an example of a storage unit.

The network interface 17 implements various information communication protocols according to the network form. The network interface 17 connects the ultrasonic diagnostic apparatus 1 and other devices such as the external image managing apparatus 60 and the image processing apparatus 70 according to these various protocols. An electrical connection or the like via an electronic network is applied to this connection. In the present embodiment, the electronic network means an entire information communication network using telecommunications technology, which includes a wired/wireless hospital backbone local area network (LAN), an Internet network, as well as a telephone communication line network, an optical fiber communication network, a cable communication network, a satellite communication network, or the like.

Further, the network interface 17 may implement various protocols for non-contact wireless communication. In this case, the image processing apparatus 10 can directly transmit and receive data to and from the ultrasonic probe 20, for example, without going through a network. The network interface 17 is an example of a network connection unit.

The control circuitry 18 may refers to a processor such as a dedicated or general-purpose CPU (central processing unit), an MPU (microprocessor unit), a GPU (Graphics Processing Unit), or the like, as well as an ASIC, a programmable logic device, or the like. The programmable logic device is, for example, a simple programmable logic device (SPLD), a complex programmable logic device (CPLD), and a field programmable gate array (FPGA).

Further, the control circuitry 18 may be constituted by a single circuit or a combination of independent circuit elements. In the latter case, the main memory 19 may be provided individually for each circuit element, or a single main memory 19 may store programs corresponding to the functions of the circuit elements. The control circuitry 18 is an example of a processor.

The main memory 19 is constituted by a semiconductor memory element such as a random-access memory (RAM), a flash memory, a hard disk, an optical disk, or the like. The main memory 19 may be constituted by a portable medium such as a universal serial bus (USB) memory and a digital video disk (DVD). The main memory 19 stores various processing programs (including an operating system (OS) and the like besides the application program) applied to the control circuitry 18 and data necessary for executing the programs. In addition, the OS may frequently use graphics when displaying information on the display 40 to the operator, and may include a graphical user interface (GUI) that enables the input interface 30 to perform basic operations. The main memory 19 is an example of a storage unit.

The ultrasonic probe 20 includes microscopic transducers (piezoelectric elements) on the front surface portion that transmits and receives ultrasonic waves to a region covering a scan target, for example, a region covering a lumen. Each transducer is an electroacoustic transducer, which has a function of converting electric pulses into ultrasonic pulses at the time of transmission and a function of converting reflected waves to electric signals (reception signals) at the time of reception. The ultrasonic probe 20 is configured to be small and lightweight, and is connected to the image processing apparatus 10 via a cable (or wireless communication).

Depending on differences in scanning system, the ultrasonic probe 20 is classified into types such as a linear type, a convex type, a sector type, etc. Further, depending on the array arrangement dimension, the ultrasonic probe 20 is classified into a 1D array probe in which transducers are arrayed in a one-dimensional (1D) manner in the azimuth direction, and a 2D array probe in which transducers are arrayed in a two-dimensional (2D) manner in the azimuth direction and in the elevation direction. The 1D array probe includes a probe in which a small number of transducers are arranged in the elevation direction.

In the present embodiment, when a 3D scan, that is, a volume scan is executed, the 2D array probe having a scan type such as the linear type, the convex type, the sector type, or the like is used as the ultrasonic probe 20. Alternatively, when the volume scan is executed, the 1D probe having a scan type such as the linear type, the convex type, the sector type, etc., and having a mechanism that mechanically oscillates in the elevation direction is used as the ultrasonic probe 20. The latter probe is also called a mechanical 4D probe.

The input interface 30 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 30 generates an input signal corresponding to the operation and outputs it to the control circuitry 18.

The display 40 is constituted by a general display output device such as a liquid crystal display or an organic light emitting diode (OLED) display. The display 40 displays various kinds of information under the control of the control circuitry 18. The display 40 is an example of a display unit.

FIG. 1 shows the image managing apparatus 60 and the image processing apparatus 70 which are external devices of the ultrasonic diagnostic apparatus 1. The image managing apparatus 60 is, for example, a digital imaging and communications in medicine (DICOM) server, and is connected to a device such as the ultrasonic diagnostic apparatus 1 such that data can be transmitted and received via the network N. The image managing apparatus 60 manages a medical image such as an ultrasonic image generated by the ultrasonic diagnostic apparatus 1 as the DICOM file.

The image processing apparatus 70 is connected to devices such as the ultrasonic diagnostic apparatus 1 and the image managing apparatus 60 such that data is transmitted and received via the network N. An Example of the image processing apparatus 70 includes a workstation that performs various image processing on the ultrasonic image generated by the ultrasonic diagnostic apparatus 1 and a portable information processing terminal such as a tablet terminal. It should be noted that the image processing apparatus 70 is an offline apparatus and may be an apparatus capable of reading an ultrasonic image generated by the ultrasonic diagnostic apparatus 1 via a portable storage medium.

Subsequently, an operation of the ultrasonic diagnostic apparatus 1 provided with the image processing apparatus 10 will be described.

Figure 7:
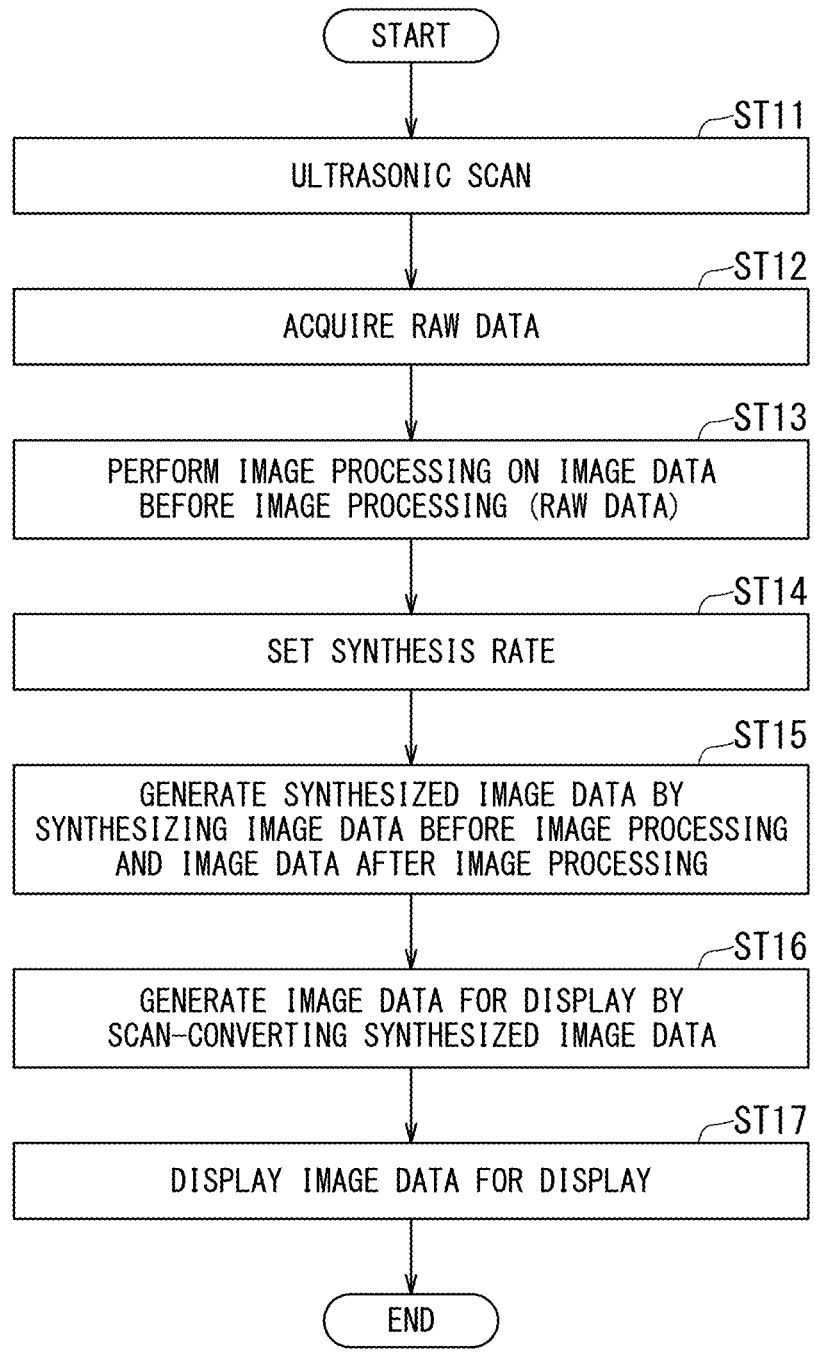
FIG. 7 is a flowchart showing an example of an operation of the ultrasonic diagnostic apparatus provided with the image processing apparatus according to the first embodiment.

FIG. 7 is a flowchart showing an example of an operation of the ultrasonic diagnostic apparatus 1 provided with the image processing apparatus 10. In FIG. 7, reference numerals with numbers attached to "ST" indicate each step of the flowchart.

The control circuitry 18 of the image processing apparatus 10 receives examination order information from, for example, an examination requesting apparatus (not shown) such as hospital information systems (HIS). The control circuitry 18 then receives an instruction to start an ultrasonic scan of the echocardiography via the input interface 30. The control circuitry 18 controls the T/R circuit 11, the B-mode processing circuit 12, the Doppler processing circuit 13, the display controlling circuit 15, and the like, thereby starting the ultrasonic scan using the ultrasonic probe 20 (step ST11). The control circuitry 18 can also display the live ultrasonic image data of each frame on the display 40.

The B-mode processing circuit 12 (or the Doppler processing circuit 13) receives echo data from the receiving circuit, performs logarithmic amplification, envelope detection processing, and the like, and acquires B-mode data in which the signal strength is expressed by the brightness of the luminance as raw data (step ST12).

The image processing circuit 14 performs image processing such as speckle removal processing on the raw data (image data before the image processing) acquired in step ST12 (step ST13). The image processing according to step ST13 is as described with reference to FIGS. 2 and 3 and the like.

The image processing circuit 14 sets a synthesis rate for synthesizing the image data before the image processing acquired in step ST12 and the image data after the image processing generated in step ST13 (step ST14). The synthesis rate is changed for each image portion divided in the depth direction. When changing the synthesis rate in consideration of the attenuation of ultrasonic waves, the image processing circuit 14 sets at least one of the settings regarding the direction (depth direction, channel direction, etc.) of dividing the image portions, the number of the divided image portions, and the synthesis rate, in accordance with at least one of the conditions regarding the frequency of the transmitted ultrasonic waves and whether a scan region (imaging target) includes a structure having a large attenuation.

Then, the image processing circuit 14 synthesizes the image data before the image processing and the image data after the image processing according to the synthesis rate set in step ST14, thereby generating synthesized image data (step ST15).

The display controlling circuit 15 generates image data for display by scan-converting the synthesized image data generated in step ST15 (step ST16). The display controlling circuit 15 displays the image data for display generated in step ST16 on the display 40 (step ST17). An example of the image displayed by step ST17 is shown in FIG. 6B.

The case where the image processing apparatus 10 performs image processing by performing the multiresolution analysis on the image data before scan conversion has been described. However, it is not limited to that case. For example, the image processing apparatus 10 may perform image processing by performing the multiresolution analysis on the image data after scan conversion.

As described above, according to the image processing apparatus 10, even if there is a difference in images in a predetermined direction (e.g., in the depth direction), it is possible to provide an image that has been subjected to entirely uniform image processing. This is because the synthesis rate is adjusted according to the depth.

Second Embodiment

The image processing and synthesizing processing such as the speckle removal processing described above can also be performed by an external apparatus of the ultrasonic diagnostic apparatus 1.

Figure 8:
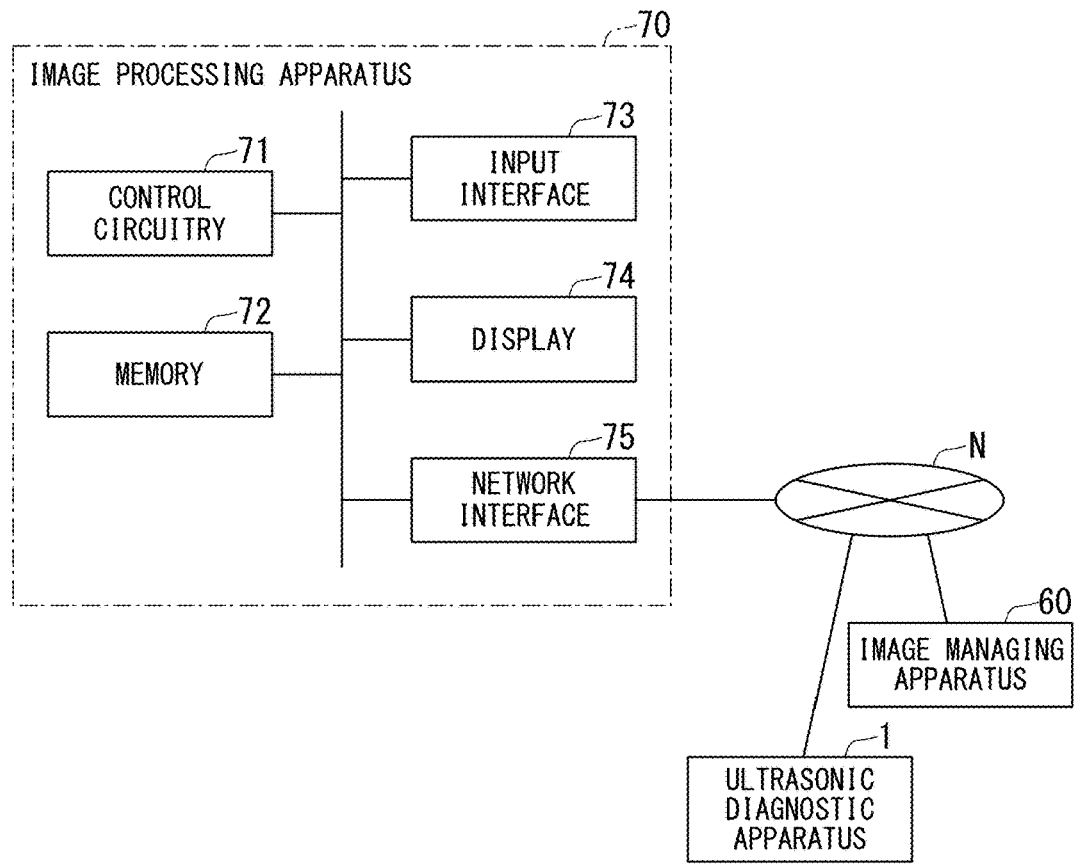
FIG. 8 is a schematic view showing a configuration of an image processing apparatus according to the second embodiment.

FIG. 8 is a schematic view showing a configuration of an image processing apparatus according to the second embodiment.

FIG. 8 shows an image processing apparatus 70 according to the second embodiment. The image processing apparatus 70 is a medical image managing apparatus (image server), a workstation, an image interpretation terminal, or the like, and is provided on a medical image system connected via a network N. The image processing apparatus 70 may be an offline apparatus.

The image processing apparatus 70 includes control circuitry 71, a memory 72, an input interface 73, a display 74, and a network interface 75. Configurations of the control circuitry 71, the memory 72, the input interface 73, the display 74, and the network interface 75 are the same as those of the control circuitry 18, the main memory 19, the input interface 30, the display 40, and the network interface 17 shown in FIG. 1 respectively, so their description will be omitted.

Subsequently, functions of the image processing apparatus 70 will be described.

Figure 9:
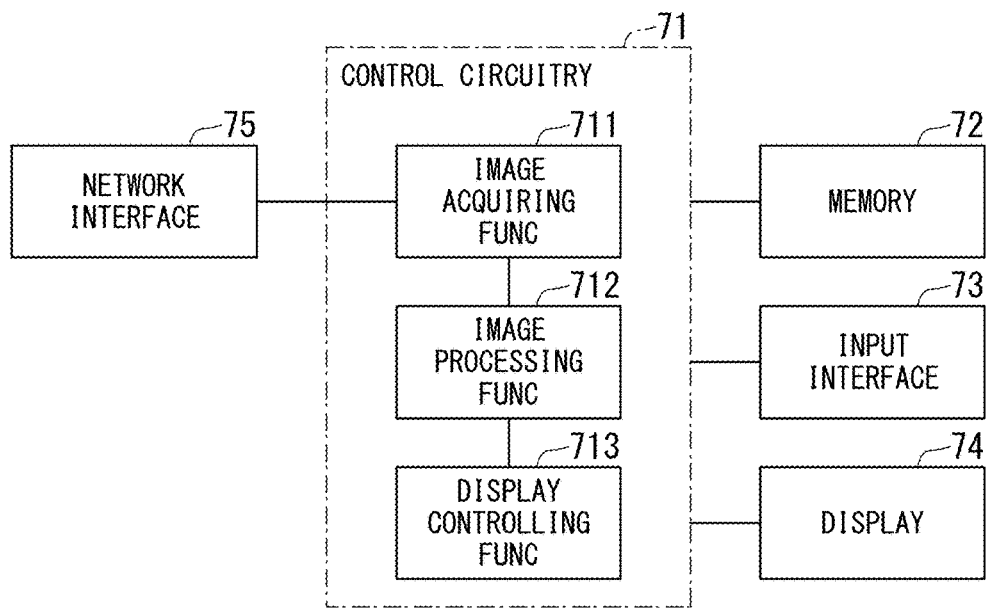
FIG. 9 is a block diagram showing functions of the image processing apparatus according to the second embodiment.

FIG. 9 is a block diagram showing functions of the image processing apparatus 70.

The control circuitry 71 realizes an image acquiring function 711, an image processing function 712, and a display controlling function 713 by executing a program stored in the memory 72. It should be noted that all or a part of the functions 711 to 713 is not limited to the case where it is realized by executing the program of the image processing apparatus 70. In some cases, the image processing apparatus 70 may be provided as a circuit such as an ASIC.

The image acquiring function 711 includes a function of acquiring the raw data depicting an inside of a subject and being acquired by an ultrasonic scan, as the image data before the image processing, from the image managing apparatus 60 or the ultrasonic diagnostic apparatus 1 via the network interface 75. The image acquiring function 711 is an example of an image acquiring unit.

Since the image processing function 712 and the display controlling function 713 have the same functions as the image processing circuit 14 and the display controlling circuit 15 shown in FIG. 1, their description will be omitted. The image processing function 712 is an example of an image processing unit, and the display controlling function 713 is an example of a display controlling unit.

As described above, according to the image processing apparatus 70, even if there is a difference in images in a predetermined direction (e.g., in the depth direction), it is possible to provide an image that has been subjected to entirely uniform image processing by adjusting the synthesis rate according to the depth, similar to the image processing apparatus 10.

According to at least one embodiment described above, it is able to provide ultrasonic image data suitable for diagnosis.

While certain embodiments have been described, these embodiments have been presented by way of example only, and are not intended to limit the scope of the inventions. Indeed, the novel methods and systems described herein may be embodied in a variety of other forms; furthermore, various omissions, substitutions, changes, and combinations of embodiments in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to
acquire image data depicting an inside of a subject acquired by an ultrasonic scan,
divide the image data into image portions, and
perform image processing on the image data, thereby synthesizing the image data before the image processing and image data after the image processing by changing a synthesis rate for each of the divided image portions.

2. The image processing apparatus according to claim 1, wherein
the processing circuitry is further configured to synthesize the image data before the image processing and the image data after the image processing by changing the synthesis rate for each image portion divided in a depth direction.

3. The image processing apparatus according to claim 2, wherein
the processing circuitry is further configured to make the synthesis rate of the image data after the image processing different between a deep image portion and a shallow image portion.

4. The image processing apparatus according to claim 3, wherein
the processing circuitry is further configured to make the synthesis rate of the deep image portion of the image data after the image processing smaller than that of the shallow image portion.

5. The image processing apparatus according to claim 1, wherein
the processing circuitry is further configured to synthesize the image data before the image processing and the image data after the image processing by changing the synthesis rate for each image portion divided in a direction orthogonal to a depth direction.

6. The image processing apparatus according to claim 1, wherein
the processing circuitry is further configured to set at least one of settings regarding a direction of dividing the image portions, a number of the divided image portions, and the synthesis rate in accordance with at least one of conditions regarding a frequency of transmitted ultrasonic waves and an imaging target.

7. The image processing apparatus according to claim 1, wherein
the processing circuitry is further configured to perform speckle removal processing as the image processing, and hierarchically decompose the image data before the image processing by a multiresolution analysis.

8. An ultrasonic diagnostic apparatus comprising:
processing circuitry configured to
acquire image data depicting an inside of a subject acquired by an ultrasonic scan,
divide the image data into image portions, and
perform image processing on the image data, thereby synthesizing the image data before the image processing and image data after the image processing by changing a synthesis rate for each of the divided image portions.

* * * * *